(12) United States Patent
Carda et al.

(10) Patent No.: US 7,993,003 B2
(45) Date of Patent: Aug. 9, 2011

(54) COMPUTERIZED METHOD FOR COLORBLINDNESS TESTING

(75) Inventors: Dan D. Carda, Tucson, AZ (US); Johan T. W. Van Dalen, Tucson, AZ (US)

(73) Assignee: Eye Care and Cure Pte. Ltd, Singapore (SG)

( * ) Notice: Subject to any disclaimer, the term of this patent is extended or adjusted under 35 U.S.C. 154(b) by 221 days.

(21) Appl. No.: 12/359,148

(22) Filed: Jan. 23, 2009

(65) Prior Publication Data

US 2010/0188639 A1    Jul. 29, 2010

(51) Int. Cl.
*A61B 3/02* (2006.01)
(52) U.S. Cl. .................................... 351/242; 351/239
(58) Field of Classification Search .............. 351/242, 351/239, 222
See application file for complete search history.

(56) References Cited

U.S. PATENT DOCUMENTS

| | | | |
|---|---|---|---|
| 6,210,006 B1 | 4/2001 | Menozzi | |
| 6,851,809 B1 | 2/2005 | Sachtler | |
| 7,264,356 B2 * | 9/2007 | Jones et al. | 351/242 |
| 2006/0033880 A1 * | 2/2006 | Korneluk | 351/242 |
| 2006/0209258 A1 * | 9/2006 | Nareppa et al. | 351/242 |
| 2007/0182755 A1 | 8/2007 | Jones et al. | |
| 2009/0005884 A1 * | 1/2009 | Ikegami et al. | 700/18 |

FOREIGN PATENT DOCUMENTS

JP   2006-55202   * 3/2006

OTHER PUBLICATIONS

JP 2006-55202 translation, Mar. 2, 2006.*
International Search Report and Written Opinion dated Apr. 20, 2010.

* cited by examiner

*Primary Examiner* — Timothy J Thompson
(74) *Attorney, Agent, or Firm* — Dale F. Regelman; Quarles & Brady LLP

(57) ABSTRACT

A computer implemented method to form, display, and evaluate, a test for colorblindness, wherein the method selects one or more test images, displays those test images seriatim to a test subject using a visual display device. A response is received from the test subject to each of the displayed test images. Each response is compared to a nominal test subject response associated with the displayed test image. The type and number of test images displayed is determined based on the test subject's responses.

17 Claims, 9 Drawing Sheets

D-15 Colour Arrangement

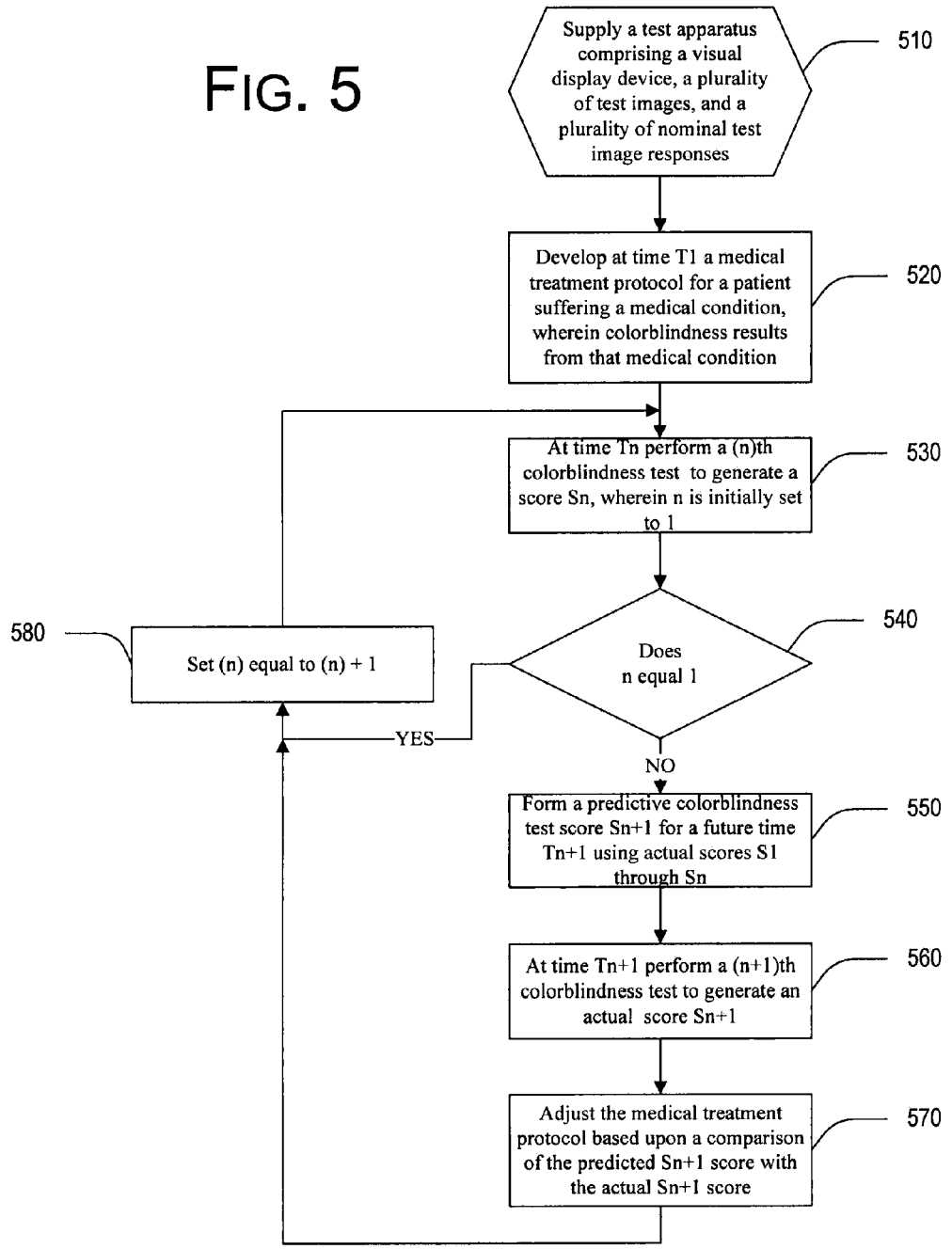

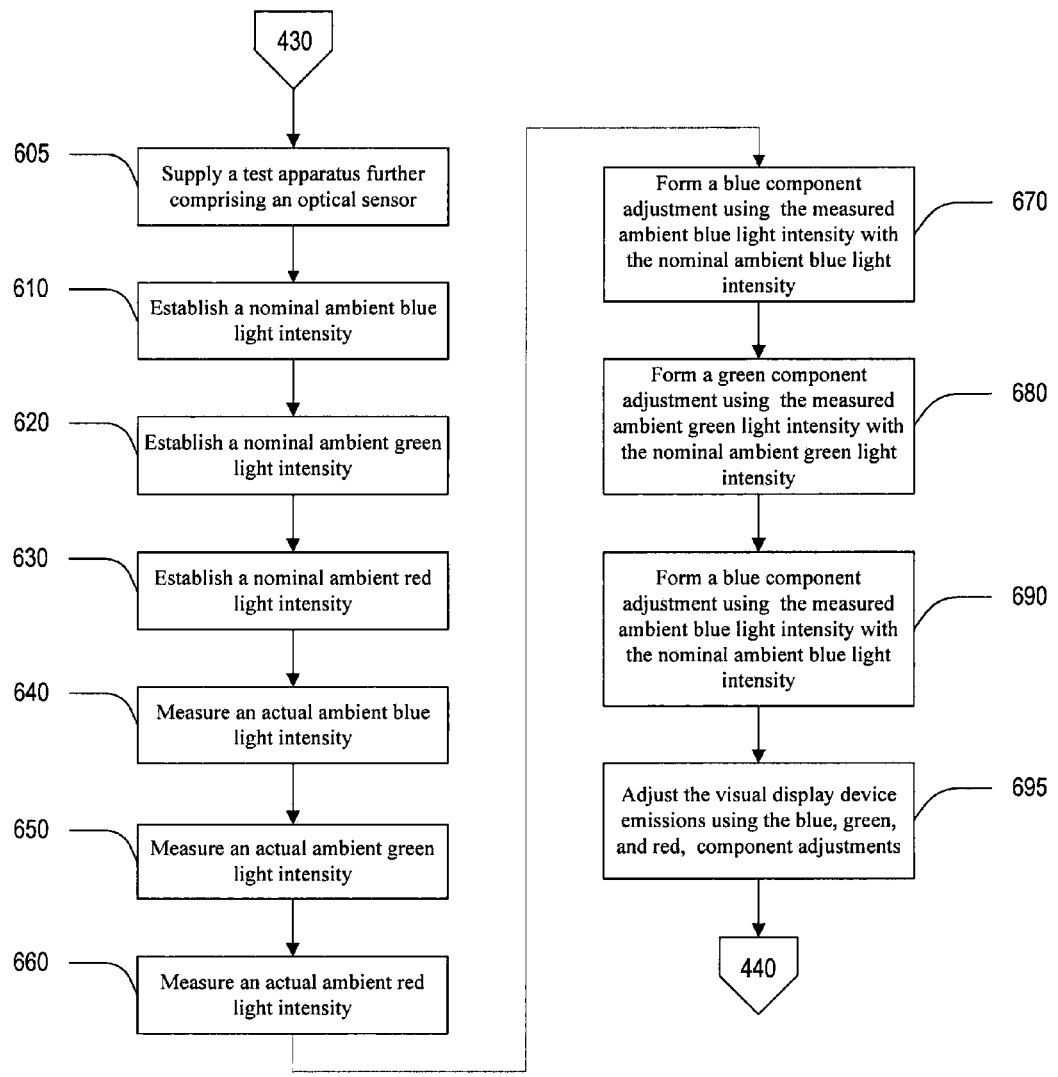

COMPUTERIZED METHOD FOR COLORBLINDNESS TESTING

BACKGROUND

The present invention relates generally to testing for color blindness, and more particularly to computerized color vision deficiency testing.

The importance of visually detecting color has increased dramatically with the advent of technology. Color coded computer information, color applications for safety, color comparison test mechanisms, and other needs have created occupational requirements for color vision. As an example, some occupations which now require verified normal color vision include aircraft pilots, dental lab technicians, pharmacists, electricians, lifeguards, and weather analysts. Thus, accurately detecting color deficiencies is important to both individuals working in these fields and those that rely on them to fulfill their duties accurately and safely.

One test commonly used to determine color vision deficiency is the Ishihara color test. The Ishihara color test consists of a number of color plates having a circle of dots of random color and size. Within the circle, some of the dots form a number that is visible to a person with normal color vision, but is invisible to a person having a color deficiency. FIG. 1A depicts an example of a Ishihara color test plate having the number 12 in a different color then the background dots. An outline of the number has been provided for illustrative purposes only. The full test consists of thirty-eight plates.

The Ishihara color test is limited in that it is designed to only detect red-green color deficiency. To determine if a patient also suffers from a blue-yellow vision deficiency a second test must be used. Further, the accuracy of the test depends heavily on the ambient lighting and the condition of the test plates. The test plates are prone to fading and must be kept out of the light except when in use. The test plates can additionally be damaged through contamination, particularly by fingerprints.

Another commonly used test is the HRR test. Unlike the Ishihara test, the HRR it is able to screen for both red-green and blue-yellow vision deficiencies. The HRR test comprises plates having dots of random color and size and includes common shapes as well as patterns that a patient is asked to trace. The first four plates are demonstrative and the next six serve to separate patients with normal color vision from those with a deficiency. The subsequent plates cover all four colors and appear increasingly bold in color to provide a qualitative manner of testing the extent of the color deficiency. FIG. 1B depicts an exemplary HRR plate having a circle and a square in a different color than the background dots. An outline of the shapes has been provided for illustrative purposes only.

Like the Ishihara color test, the accuracy of the HRR test depends heavily on ambient lighting conditions. The HRR test is designed for specific lighting and needs to be performed in a special box to ensure the results are reliable. The condition of the HRR test plates are also a factor in the tests accuracy. The HRR test plates are equally prone to fading and damaged by contamination.

A third commonly used test relies on arranging color chips rather than plates. These tests indicate not only if a patient has a color deficiency but can also provide the type and severity of the vision deficiency. These tests require a patient to arrange a number of color discs according to their similarities, starting from a fixed reference color. Patients with normal color vision will arrange the color chips from blue through green, yellow, orange and red according to the hue circle. However, individuals with color deficiencies will have difficulty with arranging the color chips in the right order and there will be some crossovers in the hue circle, the direction of the cross over indicating the type of colorblindness (i.e., deutan, tritan, or protan). Two common color chips tests are the Farnsworth D-15 and the Farnsworth 100 Hue tests. FIG. 1C illustrates the hue circle of the Farnsworth D-15 test for a person with normal color vision.

The Farnsworth tests are subject to similar limitations as the Ishihara and HRR tests. Accuracy of the test depends heavily on the ambient lighting and the condition of the test chips. To prevent damage through contamination, the Farnsworth tests are sold with gloves for the patient and test administrator to wear and replacement gloves can be purchased at an additional cost. Further, the Farnsworth tests are extremely cumbersome to score. The color chips include numbers on the back to indicate the order they should be placed assuming the patient has normal color vision. Once a patient has taken a Farnsworth test, the test administrator must turn over each color chip and record the numbers on back in the order the patient placed them before the test can be scored. This process is highly time consuming.

Both the Ishihara color test and the HRR test are further limited in that an individual who is repeatedly tested will become familiar with the order of the plates and the correct answers and, therefore, increasing color vision deficiencies may not be recognized. Handling of the plates can also cause degrade their quality, increasing testing inaccuracies. Given the need to trace patterns on some of the plates, the HRR test is especially prone to damage from handling.

All three tests, the Ishihara color test, the HRR test, and the Farnsworth color chips, additionally require a test administrator to conduct the test for the patient and then score it. This consumes valuable time and increases the costs to administer the tests.

SUMMARY

In one implementation, a computer implemented method to form, display, and evaluate, a test for colorblindness is presented. One or more test images are selected and displayed seriatim to a test subject using a visual display device. A response is received from the test subject to each of the displayed test images. Each response is compared to a nominal test subject response associated with the displayed test image. The type and number of test images displayed is determined based on the test subject's responses.

In another implementation, an article of manufacture having a computer readable medium comprising computer readable program code to form, display, and evaluate, a test for colorblindness is presented. The computer readable program code includes a series of computer readable program steps to effect selecting one or more test images, displaying those one or more test images seriatim on a visual display device, receiving a test subject response to each of the displayed test images, comparing each test subject response to a nominal response associated with the displayed test image, and determining the type and number of test images displayed based on the test subject responses.

Another implementation, a computer program product encoded in a computer readable medium and usable with a programmable computer processor to form, display, and evaluate, a test for colorblindness is presented. The computer program product includes computer readable program code that causes a programmable processor to select one or more test images, display those one or more test images seriatim on a visual display device, receive a test subject response to each of the displayed test images, compare each test subject response to a nominal response associated with the displayed test image, and determine the type and number of test images displayed based on the test subject responses.

BRIEF DESCRIPTION OF THE DRAWINGS

Implementations of the invention will become more apparent from the detailed description set forth below when taken in conjunction with the drawings, in which like elements bear like reference numerals.

FIG. 5 is a block diagram of an exemplary method of using two or more test scores to determine a predictive test score at some future time according to the present invention.

FIG. 6 is a block diagram of an exemplary method of calibrating a visual display device to ambient lighting according to the present invention.

DETAILED DESCRIPTION

This invention is described in preferred embodiments in the following description with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of the invention may be combined in any suitable manner in one or more embodiments. In the following description, numerous specific details are recited to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

Figure 1A:
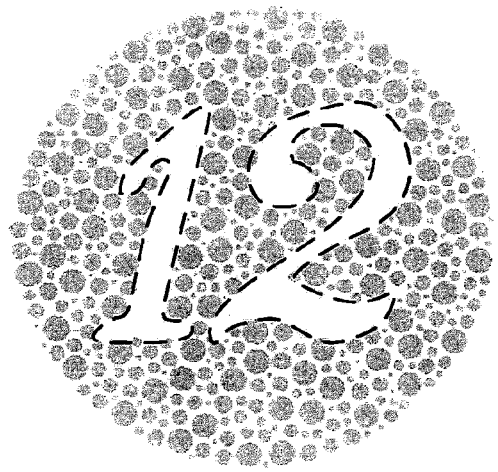
FIGS. 1A, 1B, and 1C, depict different types of colorblindness tests.
Figure 1B:
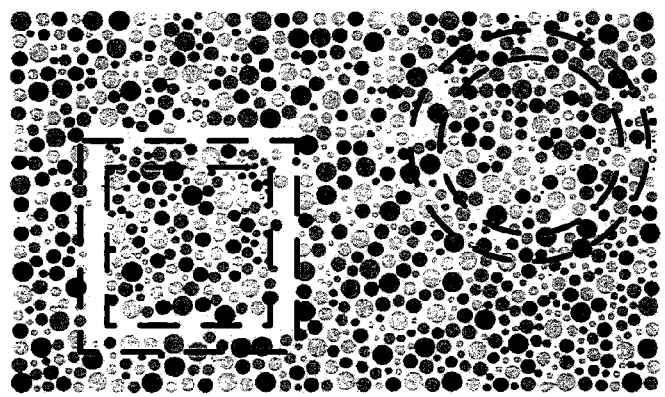
Figure 1C:
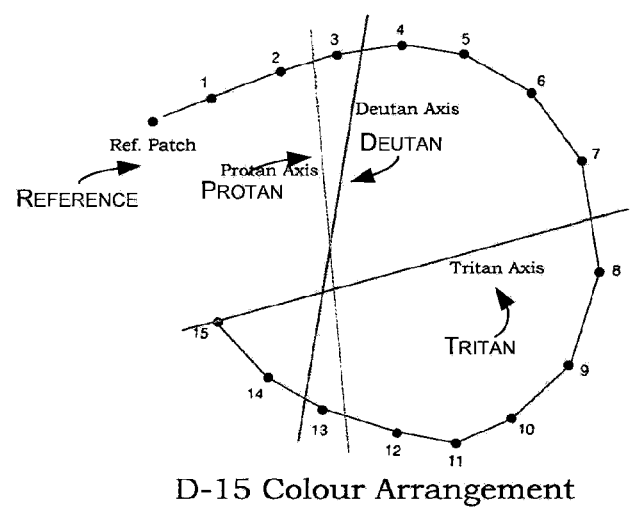
Figure 2A:
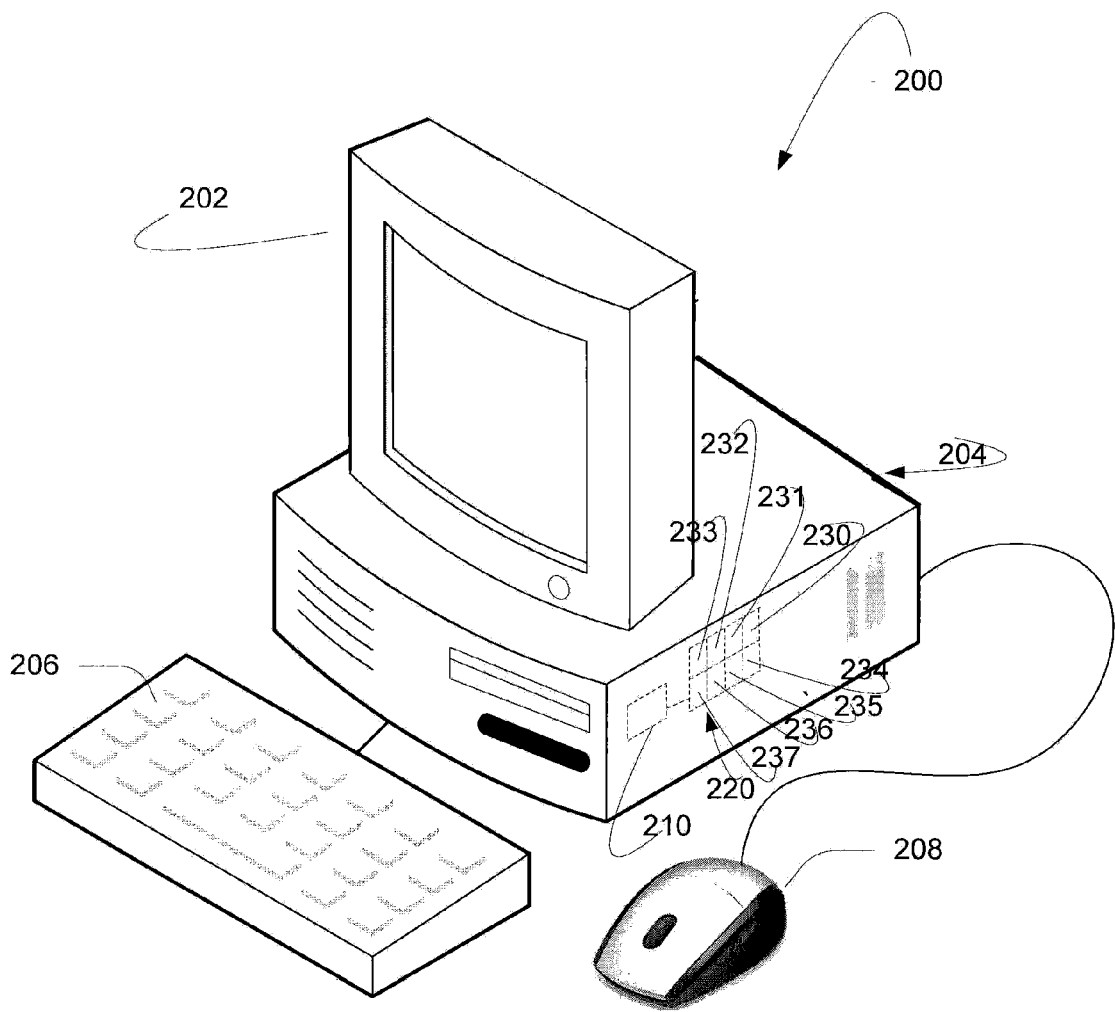
FIG. 2A depicts a first embodiment of Applicant's apparatus for use with the present invention.

Turning to FIG. 2A, Applicant's test apparatus 200 for use with the present invention is illustrated. In the illustrated embodiment of FIG. 2A; the test system comprises a computing device 204, a visual display device 202, and data input device, such as for example and without limitation, a keyboard 206 and/or a mouse 208. Computing device 204 comprises a programmable processor 204, a computer readable medium 220, and computer readable program code 230 encoded in the computer readable medium 220. In certain embodiments, computing device 204, visual display device 202, and data input device are combined into a single handheld device.

In the illustrated embodiment of FIG. 2A, test apparatus 200 further comprises a plurality of test images 231 encoded in computer readable medium 230, a low likelihood of colorblindness threshold 232 encoded in computer readable medium 230, a high likelihood of colorblindness threshold 233 encoded in computer readable medium 230, a plurality of nominal test image responses 234 encoded in computer readable medium 230 wherein a nominal test object response is associated with each test image comprising the plurality of test images 231, a nominal ambient blue light component intensity 235 encoded in computer readable medium 230, a nominal ambient green light component intensity 236 encoded in computer readable medium 230, and a nominal ambient red light component intensity 237 encoded in computer readable medium 230.

In certain embodiments, visual display device 202 comprises a liquid crystal display (LCD) display, or a plasma display. In other embodiments, visual display device 202 comprises a video projector and screen.

In certain embodiments, visual display device 202 is calibrated to the ambient light conditions. For example and referring now to FIG. 2B, test apparatus 250 comprises the elements of test apparatus 200 (FIG. 2A), and further comprises optical sensor 240.

In certain embodiments, such a calibration process is performed by analyzing the wavelength and intensity of the ambient light projected onto visual display device 202. In certain embodiments, optical sensor 240 determines the intensity of ambient light at wavelengths of between about 450 to about 495 nanometers, i.e., a measured blue light component intensity. Optical sensor provides that measured ambient blue light component intensity to processor 210. Processor compares the measured ambient blue light component intensity with a nominal ambient blue light component intensity 235, and using that comparison adjusts the intensity of light emitted from visual display device at wavelengths between about 450 to about 495 nanometers.

In certain embodiments, optical sensor 240 determines the intensity of ambient light at wavelengths of between about 495 to about 570 nanometers, i.e., a measured ambient green light component intensity. Optical sensor provides that measured ambient green light component intensity to processor 210. Processor compares the measured ambient green light component intensity with a nominal ambient green light component intensity 236, and using that comparison adjusts the intensity of light emitted from visual display device at wavelengths between about 495 to about 570 nanometers.

In certain embodiments, optical sensor 240 determines the intensity of ambient light at wavelengths of between about 625 to about 740 nanometers, i.e., a measured ambient red light component intensity. Optical sensor provides that measured ambient red component intensity to processor 210. Processor compares the measured ambient red light component intensity with a nominal ambient red light component intensity 237, and using that comparison adjusts the intensity of light emitted from visual display device at wavelengths between about 625 to about 740 nanometers.

In certain embodiments, the calibration process is performed prior to each test. In other embodiments, the calibration process is performed prior to each image being displayed. In yet other embodiments, the calibration process is performed at given time intervals. In certain embodiments, visual display device 202 is self calibrating using optical sensor 240. In other embodiments, visual display device 202 is calibrated manually.

In certain embodiments, data input device 206 comprises a touch screen. In such embodiments, by way of example and not by way of limitation, a test subject may trace a shape or path shown in a test image on visual display device 202 using a stylus or a finger. In certain embodiments, data input device comprises a receiver capable of receiving voice commands. In such embodiments, by way of example and not by way of limitation, a user's vocalized response to the test image on visual display device 202 may be received by a microphone.

In certain embodiments, computer system 200 includes an audio component. In such an embodiment, the test subject may listen to instructions and provide test responses using a microphone.

Figure 3A:
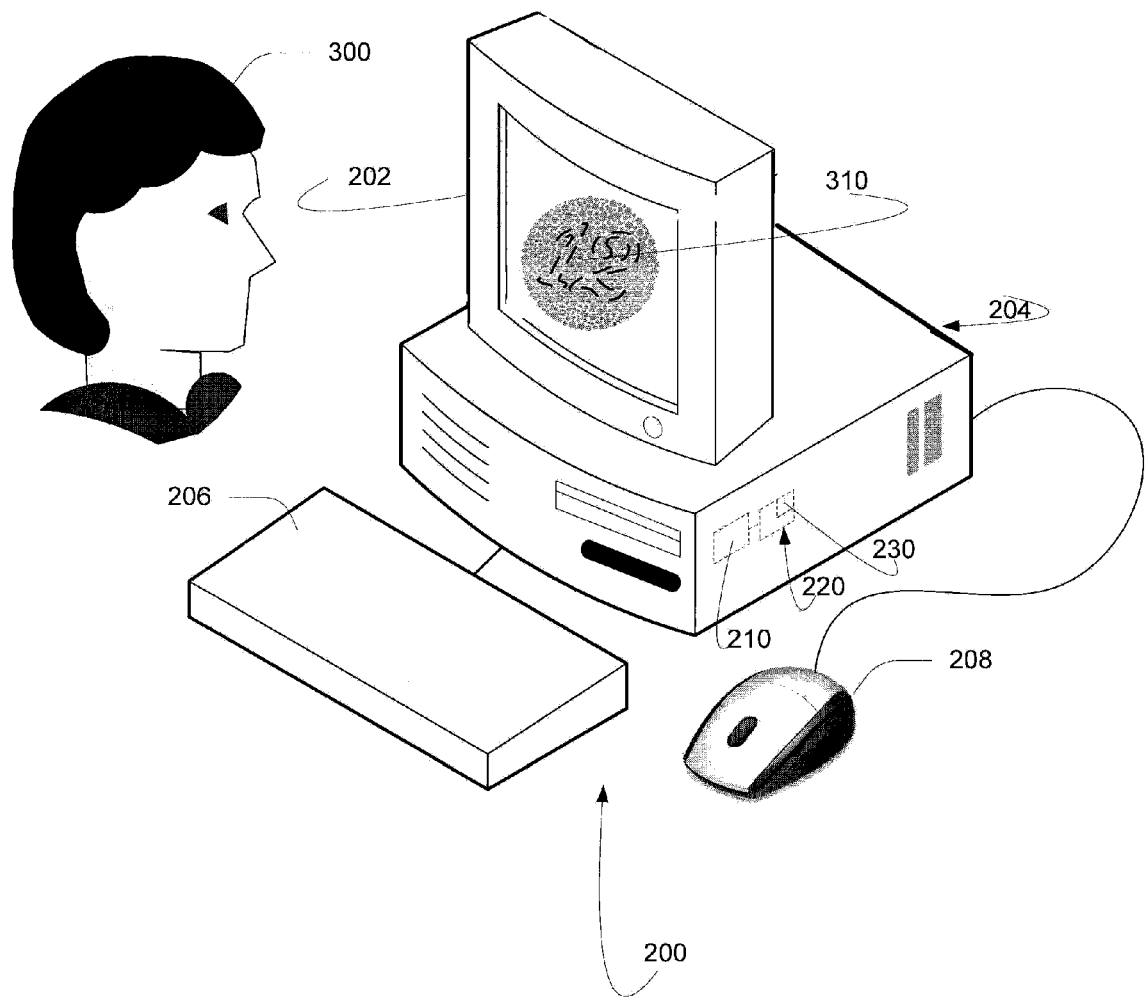
FIG. 3A depicts the computer system of FIG. 2A being used by a test subject taking a colorblindness test according to the present invention.

FIG. 3A illustrates a test subject 300 using the test system apparatus of FIG. 2A. In the illustrated embodiment of FIG. 3A, visual display device 202 displays an image 310 in accordance with the present invention. After viewing image 310, test subject 300 can input a response using keyboard 206 or mouse 208.

Figure 3B:
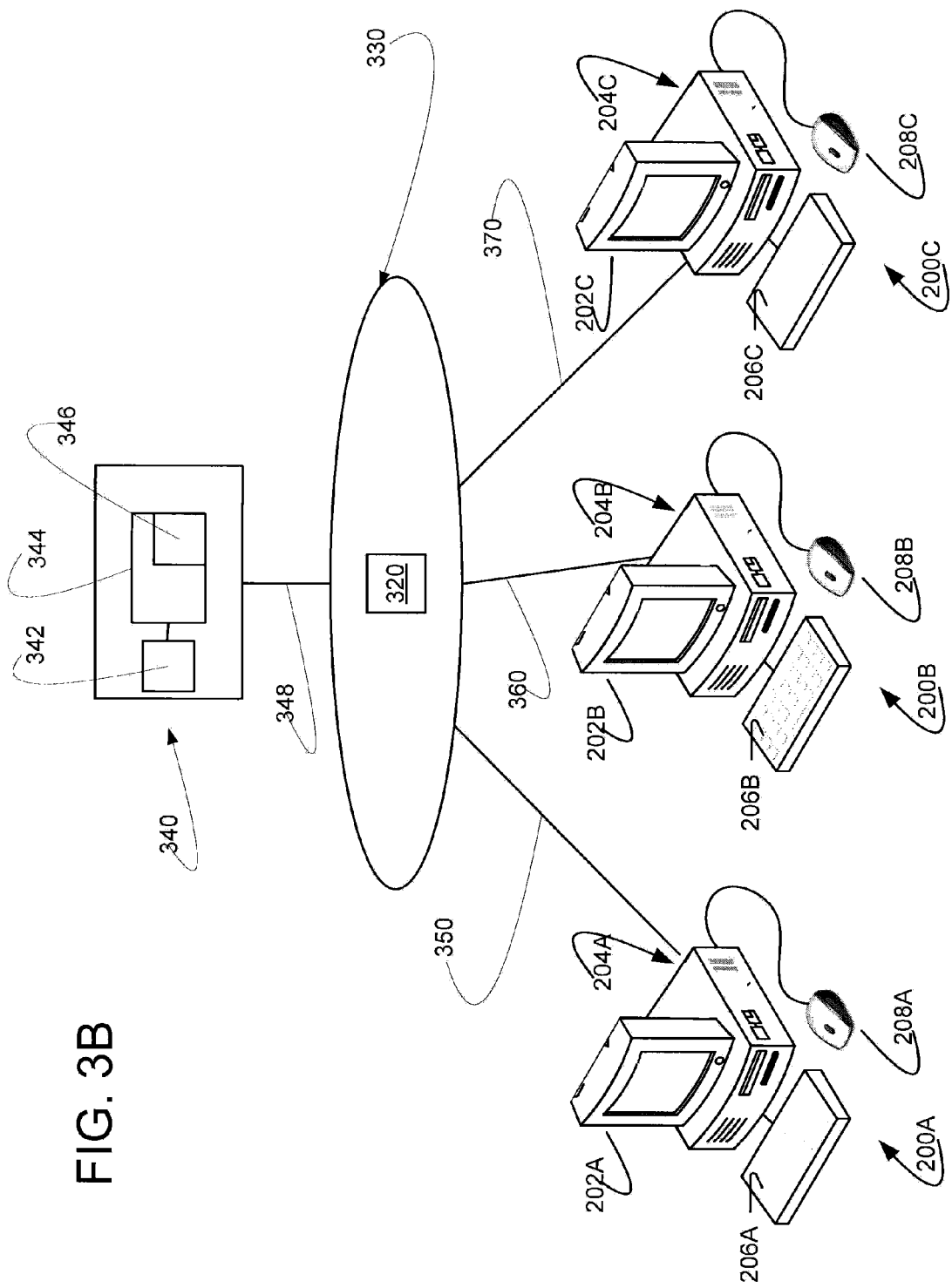
FIG. 3B illustrates a plurality of test apparatus being interconnected via a network to a central server.

FIG. 3B shows a plurality of test apparatus stations 200A, 200B, and 200C, interconnected with a server 340 via communication fabric 330. In the illustrated embodiment of FIG. 3B, test apparatus stations 200A, 200B, and 200C, communicate with storage controller 760 through a data communication fabric 330. In certain embodiments, fabric 330 comprises one or more data switches 320.

Test Apparatus 200A is interconnected with fabric 330 via communication link 350. Test Apparatus 200B is interconnected with fabric 330 via communication link 360. Test Apparatus 200C is interconnected with fabric 330 via communication link 370.

In certain embodiments, one or more of communication links 350, 360, and/or 370, utilize a Small Computer Systems Interface ("SCSI") communication protocol running over a Fibre Channel ("FC") physical layer. In certain embodiments, one or more of communication links 350, 360, and/or 370, utilize other communication protocols, such as Infiniband, Ethernet, or Internet SCSI ("iSCSI"). In certain embodiments, switches 320 are configured to route traffic from Test Apparatus stations 200A, 200B, and 200C directly to server 340.

In certain embodiments, each of Test Apparatus stations 200A, 200B, and 200C, is disposed in a different room in the same facility, wherein that facility comprises, without limitation, a physician's office, a hospital, a work place, a motor vehicle department office, and the like. In certain embodiments, In certain embodiments, each of Test Apparatus 200A, 200B, and 200C, is disposed in a different building, city, state, or country. In either event, each of test apparatus stations 200A, 200B, and 200C, can operate independently from one another, i.e., display different color blindness testing protocols, receive differing input responses from different test subjects, and save those input response locally. In certain embodiments, each of test apparatus stations 200A, 200B, and 200C, receive differing input responses from different test subjects, save those differing input responses locally, and provide those differing test subject responses to server 340, wherein server 340 saves the differing test subject responses in computer readable medium 344.

Figure 2B:
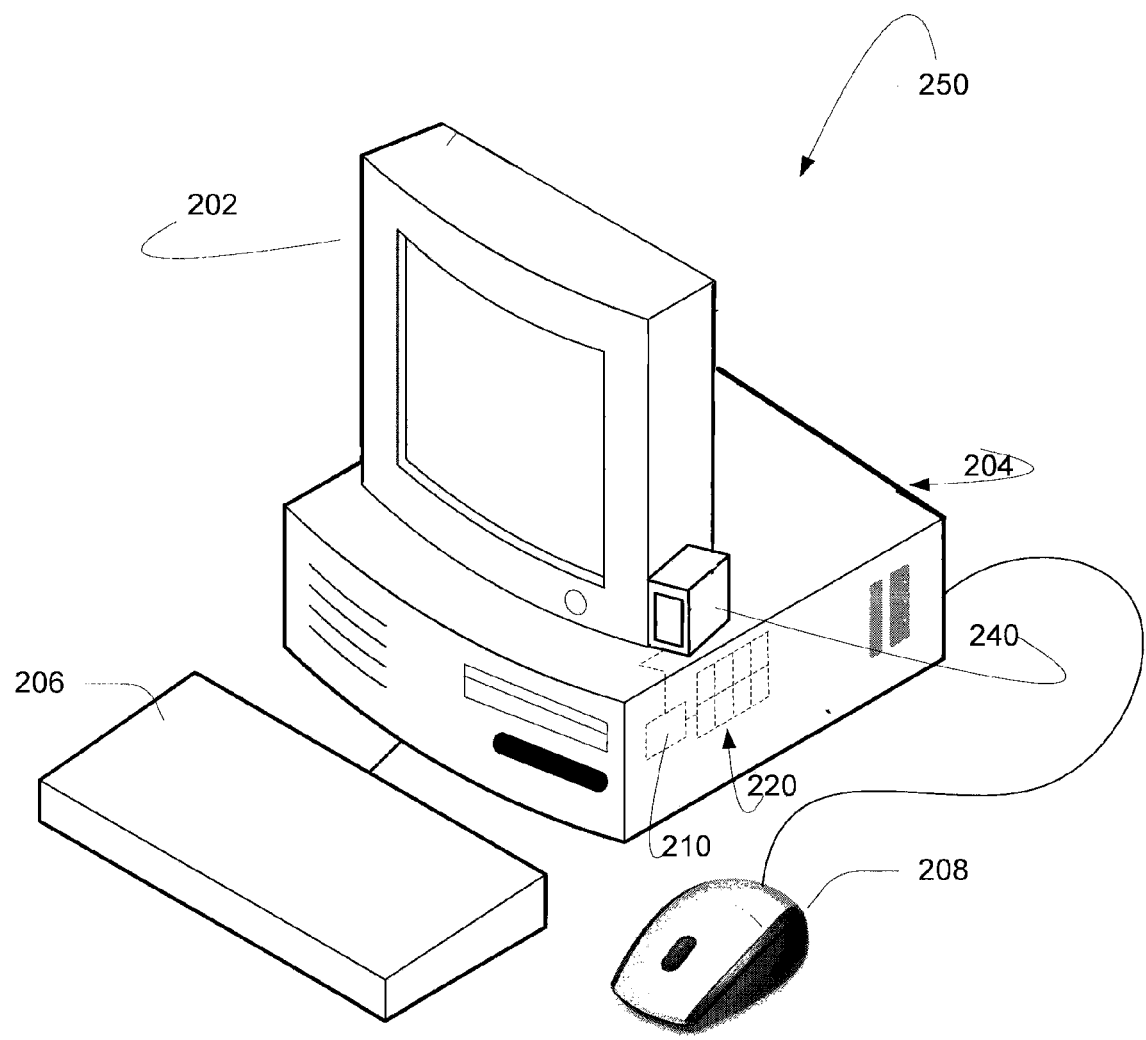
FIG. 2B depicts a second embodiment of Applicant's apparatus for use with the present invention.
Figure 4A:
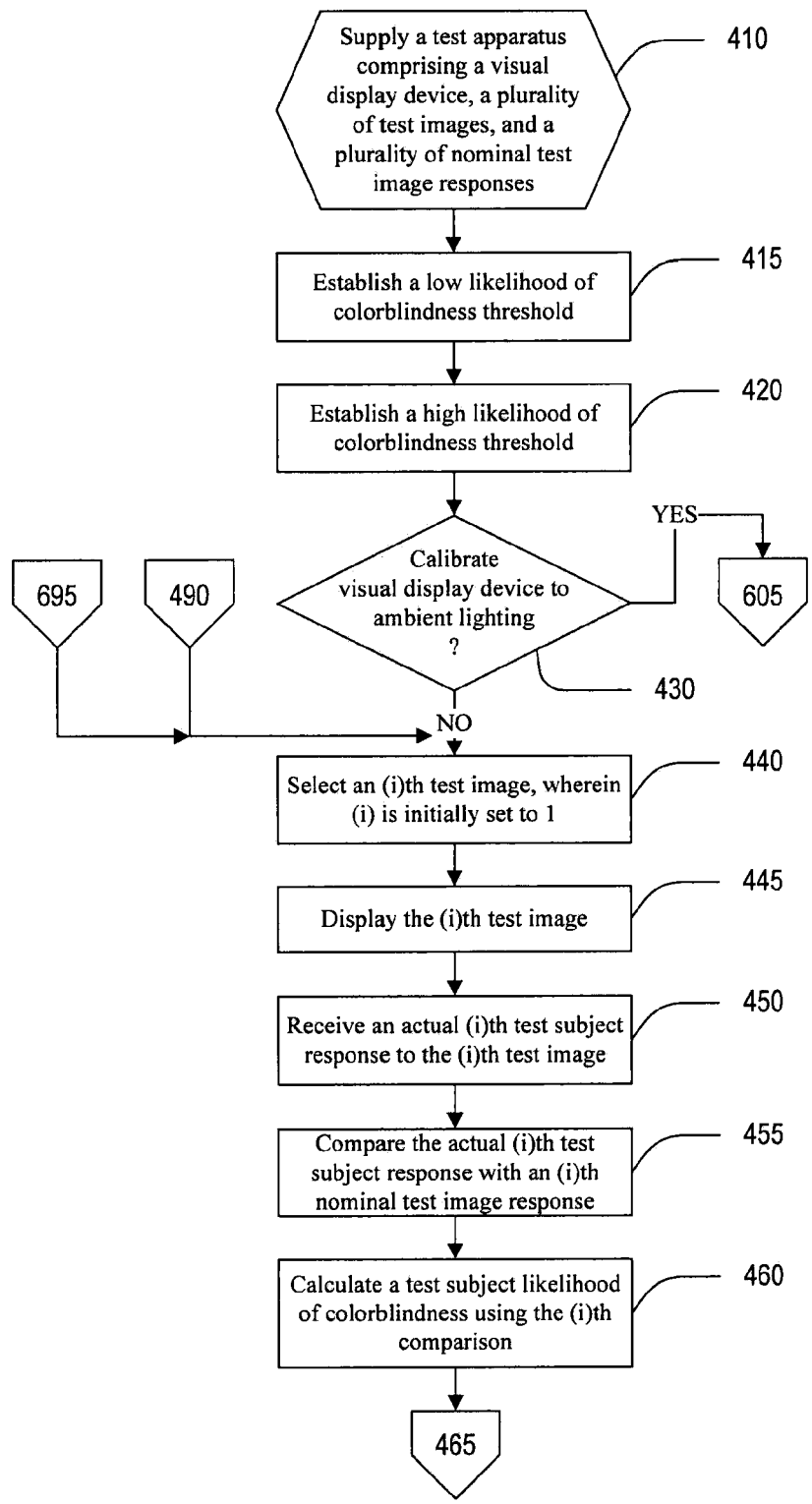
FIG. 4 is a block diagram of an exemplary method of displaying test images according to the present invention.

FIG. 4A summarizes Applicants' method using Applicants' test apparatus 200 (FIG. 2A)/250 (FIG. 2B). In block 410, the method supplies a test apparatus, such as test apparatus 200 (FIG. 2A) or test apparatus 250 (FIG. 2B), wherein that test apparatus comprises a visual display device, a plurality of test images, and an associated plurality of nominal test image responses.

In block 415, the method establishes a low likelihood of colorblindness threshold. In certain embodiments, the low likelihood of colorblindness threshold comprises a high percentage of correctly identified test images, i.e., more than ninety percent (90%) correctly identified test images. In certain embodiments, the low likelihood of colorblindness threshold comprises a percentage of correctly identified test images within a specified time interval, i.e., more than ninety percent (90%) correctly identified test images, wherein test subject responses comprising a correctly identified image were input within two minutes after the test image was first displayed.

In block 420, the method establishes a high likelihood of colorblindness threshold. In certain embodiments, the high likelihood of colorblindness threshold comprises a low percentage of correctly identified test images, i.e., less than fifty percent (50%) correctly identified test images.

In block 430, the method determines whether to calibrate the visual display device of block 410 with respect to ambient lighting. If the method elects not to calibrate the visual display device, then the method transitions from block 430 to block 440.

Alternatively, if the method elects to calibrate the visual display device with respect to ambient lighting, then the method transitions from block 430 to block 605 (FIG. 6), wherein the method in certain embodiments supplies a test apparatus, such as and without limitation test apparatus 250 (FIG. 2B) that comprises an optical sensor, such as and without limitation optical sensor 240 (FIG. 2B). In other embodiments, the method of FIG. 6 is performed manually using an optical sensor not in communication with processor 210.

In block 610, the method establishes a nominal ambient blue light intensity 235 (FIG. 2A). This nominal ambient blue light intensity 235 is encoded in computer readable medium 220 (FIG. 2A) disposed in computing device 204 (FIGS. 2A, 2B).

In block 620, the method establishes a nominal ambient green light intensity 236 (FIG. 2A). This nominal ambient green light intensity 236 is encoded in computer readable medium 220 (FIG. 2A) disposed in computing device 204 (FIGS. 2A, 2B).

In block 630, the method establishes a nominal ambient red light intensity 237 (FIG. 2A). This nominal ambient red light intensity 237 is encoded in computer readable medium 220 (FIG. 2A) disposed in computing device 204 (FIGS. 2A, 2B).

In certain embodiments, blocks 610, 620, and 630, are combined such that the method establishes a nominal ambient light intensity.

In block 640, the method measures an actual ambient blue light intensity. In certain embodiments, block 640 is performed by processor 210 (FIG. 2A) using optical sensor 240 (FIG. 2B). In other embodiments, block 640 is performed manually.

In block 650, the method measures an actual ambient green light intensity. In certain embodiments, block 650 is performed by processor 210 (FIG. 2A) using optical sensor 240 (FIG. 2B). In other embodiments, block 650 is performed manually.

In block 660, the method measures an actual ambient red light intensity. In certain embodiments, block 660 is performed by processor 210 (FIG. 2A) using optical sensor 240 (FIG. 2B). In other embodiments, block 660 is performed manually.

In certain embodiments, blocks 640, 650, and 660, are combined such that the method measures an actual ambient light intensity.

In block 670, the method forms a blue ambient light adjustment using the nominal blue ambient light intensity of block 610 and the measured ambient blue light intensity of block 640. In certain embodiments, block 670 is performed by processor 210 (FIG. 2A) using optical sensor 240 (FIG. 2B). In other embodiments, block 670 is performed manually.

In block 680, the method forms a green ambient light adjustment using the nominal green ambient light intensity of block 620 and the measured ambient green light intensity of block 650. In certain embodiments, block 650 is performed by processor 210 (FIG. 2A) using optical sensor 240 (FIG. 2B). In other embodiments, block 650 is performed manually.

In block 690, the method forms a red ambient light adjustment using the nominal red ambient light intensity of block 620 and the measured ambient red light intensity of block 650. In certain embodiments, block 690 is performed by processor 210 (FIG. 2A) using optical sensor 240 (FIG. 2B). In other embodiments, block 690 is performed manually.

In certain embodiments, blocks 670, 680, and 690, are combined such that the method forms aggregate intensity adjustment using an aggregate actual ambient light intensity and a aggregate measured ambient light intensity.

In block 695, the method adjusts the intensity of test images displayed by the visual display device of block 410 (FIG. 4A) using the blue/green/red adjustments of blocks 670, 680, and 690, or using an aggregate intensity adjustment. In certain embodiments, block 695 is performed by processor 210 (FIG. 2A). In other embodiments, block 695 is performed manually.

The method transitions from block 695 to block 440 (FIG. 4A), wherein the method selects an (i)th test image. In certain embodiments, block 440 is performed by processor 210 (FIG. 2A). In certain embodiments, the (i)th test image is selected based on whether an (i−1)th response was received. In certain embodiments, rather then selecting an (i)th test image based on the prior response, an (i)th test image is selected randomly from the plurality of test images of block 410. In other embodiments, the (i)th test image is selected based upon whether the method is currently implementing an Ishihara-type color test, a HRR-type test, or a Farnsworth-type test. In still other embodiments, an (i)th test image is selected to transition between a first test protocol, such as an Ishihara-type color test, and a second test protocol, such as a HRR-type test. In certain embodiments, such a transition from one test protocol to a second test protocol is based upon the test subject's response to an (i−1)th test image.

In block 445, the method displays on the visual display device of step 410, as optionally calibrated using the blocks recited in FIG. 6, an (i)th test image selected in block 440. In certain embodiments, the (i)th test image is displayed on a calibrated visual display device at an visual light intensity based upon measured ambient lighting. In other embodiments, the intensity of a displayed (i)th test image is refined or altered to, for example, determine a minimum intensity level at which the test subject is able to correctly identify the test image.

In certain embodiments, the method calibrates the visual display device just prior to displaying each test image. In these embodiments, block 445 includes calibrating the visual display device, as described hereinabove, prior to displaying an (i)th test image.

As indicated at block 450 the method receives an actual (i)th test subject response.

In block 455, the method compares an actual (i)th test subject response of block 450 with an (i)th nominal test image response associated with the (i)th test image. In certain embodiments, processor 210 (FIG. 2A) retrieves an (i)th nominal test image response from the plurality of nominal test images 234 (FIG. 2A) encoded in computer readable medium 220 (FIG. 2A).

In block 460, the method calculates a test subject likelihood of colorblindness using the (i)th comparison of block 455. In certain embodiments, in block 460 the method calculates a test subject likelihood of colorblindness using a comparison of a plurality of test subject responses received in comparison to a corresponding plurality of associated nominal test image responses. In certain embodiments, processor 210 performs block 460.

Figure 4B:
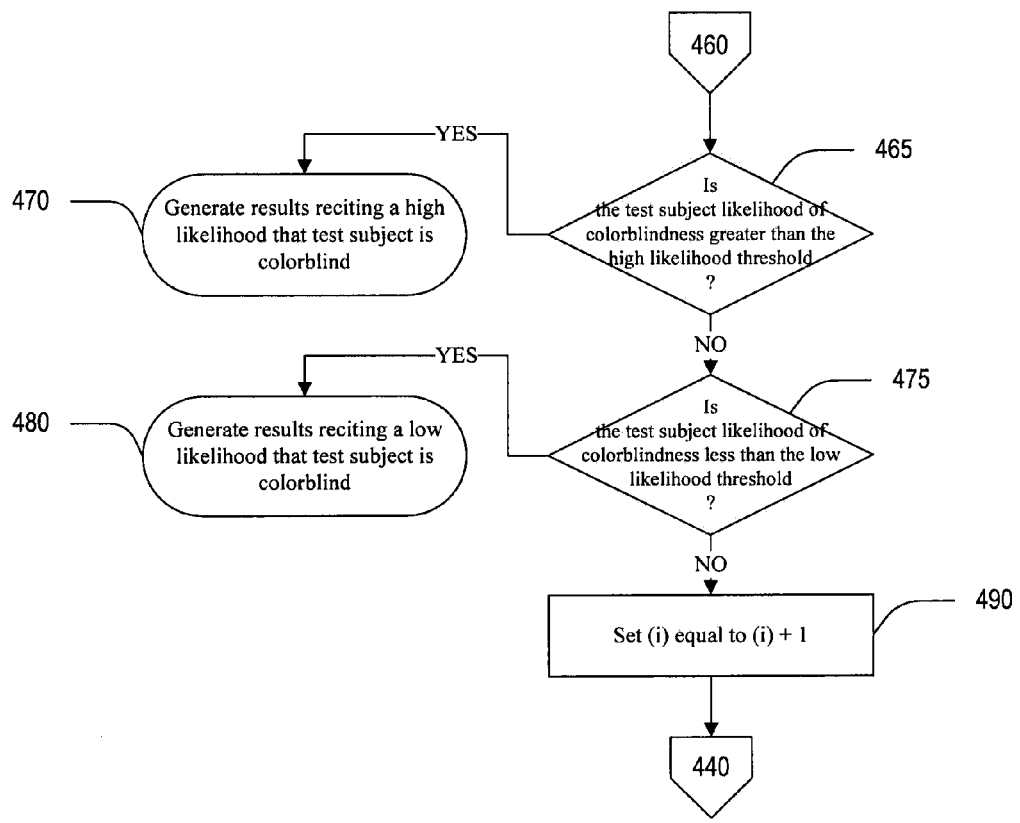

Referring now to FIG. 4B, in block 465 the method determines if the test subject likeliness of colorblindness of block 460 is greater than the high likelihood threshold of block 420. In certain embodiments, processor 210 performs block 465.

If the method determines in block 465 that the test subject likeliness of colorblindness of block 460 is greater than the high likelihood threshold of block 420, then the method transitions from block 465 to block 470 wherein the method generates test results reciting a high likelihood that the test subject is colorblind. In certain embodiments, processor 210 performs block 470.

Alternatively, if the method determines in block 465 that the test subject likeliness of colorblindness of block 460 is not greater than the high likelihood threshold of block 420, then the method transitions from block 465 to block 475 wherein the method determines if the test subject likeliness of colorblindness of block 460 is less than the low likelihood threshold of block 410. In certain embodiments, processor 210 performs block 475.

If the method determines in block 475 that the test subject likeliness of colorblindness of block 460 is less than the low likelihood threshold of block 410, then the method transitions from block 475 to block 480 wherein the method generates test results reciting a low likelihood that the test subject is colorblind. In certain embodiments, processor 210 performs block 480.

Alternatively, if the method determines in block 475 that the test subject likeliness of colorblindness of block 460 is not less than the low likelihood threshold of block 410, then the method transitions from block 475 to block 480 wherein the method increments (i) by unity, i.e., sets (i) equal to (i)+1. In certain embodiments, processor 210 performs block 490. The method transitions from block 490 to block 440 and continues as described herein.

In certain embodiments, a test score may be determined after each user response is received. By way of example, and not by way of limitation, such cases may include where a given number of test images has indicated the user does not have a color deficiency. Alternatively, such a case, by way of example, may include where the user's color deficiency is clearly diagnosed from a given number of test images.

By way of example, the method of testing colorblindness depicted in FIG. 4A, may include a total of 100 test images. In other embodiments the method of testing color blindness may include less than 100 test images. In still other embodiments the method of testing color blindness may include more than 100 test images. The first image displayed to the test taker is the initial image. The initial test image may be, for example, an Ishihara color plate where the number 16 is presented in red against a green background The test taker may respond to the image by using key board to enter a numerical value.

Based upon the first response, the second test image is determined. Where, for example, the user responded to the first test image incorrectly, the second test image may also have a red figure, this time the number 9. Where the test taker's response indicates that the test taker is having difficulty seeing the color red, test images 3 through 10 may further test for the red colorblindness to confirm the test taker's color deficiency. Test images 11 through 20 may subsequently be displayed to determine the extent of the existing color deficiency, by for example having the same red colored figure displayed at differing intensities.

Test image 21 may then test for a different color deficiency than the initial test image. For example, test image 21 may be a HRR color plate where a blue square is shown against a grey background. The test taker may respond to the image by, for example, using a stylus, or cursor to trace the shape on the display monitor. Based on the test taker's response to test image 21, test image 22 is selected. Where for example, the test taker responded correctly to test image 21, test image 22 may still test for the a blue color deficiency to verify the result. If the test taker's response to image 22 is correct, test image 23 may show the blue same shape as test image 22, but at a different intensity. Where, for example, the test taker responds to test image 23 correctly, test image 24 may test difficulty seeing, for example, the color green.

In certain embodiments, test images continued to be selected, and a test subject likelihood of colorblindness determined for each of red, green, blue, and yellow colors. In these embodiments, the method generates test results specific to each of the colors tested. Such test results may indicate, for example and without limitation, a strong red-green color deficiency but no blue-yellow color deficiency.

FIG. 5 summarizes Applicants' method to use colorblindness tests to determine a course of action for, by way of example, and not by way of limitation, treatment for a medical condition, chemical toxicity, medication toxicity, or to make an employment decision where normal color vision is a requirement.

In block 510, the method provides a colorblindness test apparatus, for example and without limitation test apparatus 200 (FIG. 2A or test apparatus 250 (FIG. 2B), wherein that test apparatus comprises a plurality of test images and a plurality of nominal test image responses.

In block 520, the method develops at a time T1 a medical treatment protocol for a patient suffering a medical condition, wherein colorblindness results from that medical condition. In certain embodiments, block 520 is performed by a physician.

In block 530, the method performs a (n)th colorblindness test to generate a (n)th score Sn, wherein (n) is initially set to 1. In certain embodiments, in block 530 the method selects and displays a total of (N) test images, wherein (N) is greater than 1. In these embodiments, the (n)th score Sn comprises a number of correctly identified test images divided by (N).

In certain embodiments, block 530 utilizes Applicants' method recited in FIGS. 4A and 4B, and as described hereinabove. In certain embodiments, block 530 further utilizes the method of FIG. 6 as described hereinabove. In certain embodiments, block 530 is performed by a processor, such as for example and without limitation processor 210, disposed in the test apparatus of block 510.

In block 540, the method determines if n equals 1. In certain embodiments, block 540 is performed by a processor, such as for example and without limitation processor 210, disposed in the test apparatus of block 510.

If the method determines in block 540 that n equals 1, then the method transitions from block 540 to block 580 and sets (n) equal to (n)+1. In certain embodiments, block 580 is performed by a processor, such as for example and without limitation processor 210, disposed in the test apparatus of block 510. The method transitions from block 580 to block 530 and continues as described herein.

Alternatively, if the method determines in block 540 that (n) does not equal 1, then the method transitions from block 540 to block 550 wherein the method forms a predictive colorblindness score for a future time Tn+1 using actual scores S1 through Sn measured at previous times T1 through Tn. In certain embodiments, block 550 is performed by a processor, such as for example and without limitation processor 210, disposed in the test apparatus of block 510.

In certain embodiments, block 550 utilizes a linear curve fitting algorithm using data points S1 through Sn to predict a future score Sn+1 at time Tn+1. In certain embodiments, block 550 utilizes a second order curve fitting algorithm using data points S1 through Sn to predict a future score Sn+1 at time Tn+1. In certain embodiments, block 550 utilizes a third order curve fitting algorithm using data points S1 through Sn to predict a future score Sn+1 at time Tn+1.

In block 560, at a time Tn+1, the method measures an actual colorblindness score Sn+1. In certain embodiments, block 560 utilizes Applicants' method recited in FIGS. 4A and 4B, and as described hereinabove. In certain embodiments, block 560 further utilizes the method of FIG. 6 as described hereinabove. In certain embodiments, block 560 is performed by a processor, such as for example and without limitation processor 210, disposed in the test apparatus of block 510.

In block 570, the method adjusts the medical treatment protocol of block 520 using a comparison of the predicted score Sn+1 with the actual score Sn+1. In certain embodiments, block 560 is performed by a processor, such as for example and without limitation processor 210, disposed in the test apparatus of block 510.

By way of example, a patient, taking a medication having a known side effect of colorblindness, is tested January 1 prior to taking the medication, and receives score $s_0$. On March 1, the patient is again tested, after having taken the medication, and receives a score $s_1$. A predictive score for June 1 is then calculated based on $s_0$ and $s_1$. Given the predictive score for June 1, a physician may decide, for example, to continue the patient on the medication, even if, for example, $s_1$ indicates the patient is suffering some color deficiency. The patient is then tested again on July 1 and a score $s_2$ is calculated. The value of $s_2$ may, for example, be the same as $s_1$. Based on $s_0$, $s_1$, and $s_2$ a predictive score is calculated for September 1. Where, for example, the predictive score for September 1 indicates that the current color deficiency will not worsen, the doctor may again decide to continue treating the patient with the medication. The patent is then tested again on September 1, after nine months of taking the medication, and a fourth score $s_3$ is obtained. The value of $s_3$ may, for example, indicate a the patient is now suffering from an increased color deficiency. Based on $s_0$, $s_1$, $s_2$, and $s_3$ a predictive score may be calculated for December 1. The predictive score may indicate that the current deficiency will worsen beyond a given threshold and the doctor may decide to alter or discontinue treatment with the medication.

In certain embodiments, individual blocks described above may be combined, eliminated, or reordered.

Instructions, such as instructions 230 (FIG. 2A) are encoded in computer readable medium 220 (FIG. 2A), wherein those instructions are executed by processor 210 (FIG. 2A) to perform one or more of blocks 415, 420, 430, 440, 445, 450, 455, 460 recited in FIG. 4A, and/or one of more of blocks 465, 470, 475, 480, and/or 490, recited in FIG. 4B, and/or one or more of blocks 510, 520, 530, 540, 550, 560, 570, and/or 580, recited in FIG. 5, and/or one or more of blocks 605, 610, 620, 630, 640, 650, 660, 670, 680, 690, and/or 695, recited in FIG. 6.

In yet other embodiments, the invention includes instructions residing in any other computer program product, where those instructions are executed by a computer external to, or internal to, a computing system to perform one or more of blocks 415, 420, 430, 440, 445, 450, 455, 460 recited in FIG. 4A, and/or one of more of blocks 465, 470, 475, 480, and/or 490, recited in FIG. 4B, and/or one or more of blocks 510, 520, 530, 540, 550, 560, 570, and/or 580, recited in FIG. 5, and/or one or more of blocks 605, 610, 620, 630, 640, 650, 660, 670, 680, 690, and/or 695, recited in FIG. 6. In either case, the instructions may be encoded in a computer readable medium comprising, for example, a magnetic information storage medium, an optical information storage medium, an electronic information storage medium, and the like. "Electronic storage media," may mean, for example and without limitation, one or more devices, such as and without limitation, a PROM, EPROM, EEPROM, Flash PROM, compactflash, smartmedia, and the like.

While the preferred embodiments of the present invention have been illustrated in detail, it should be apparent that modifications and adaptations to those embodiments may occur to one skilled in the art without departing from the scope of the present invention.

What is claimed is:

1. A computer implemented method to create, display, and evaluate, a test for colorblindness, the method comprising:
   supplying a test apparatus comprising a visual display device in communication with a computing device comprising a programmable processor, a computer readable medium, instructions encoded in said computer readable medium, a plurality of test images encoded in said computer readable medium, a plurality of nominal test image responses encoded in said computer readable medium, wherein a nominal test image response is associated with each of said plurality of test images, a low likelihood of colorblindness threshold encoded in said computer readable medium, and a high likelihood of colorblindness threshold encoded in said computer readable medium;
   displaying by said programmable processor using said visual display device an (i)th test image, wherein (i) is initially set to 1, and wherein said (i)th test image comprises one of said plurality of test images;
   receiving by said programmable processor an (i)th test subject response associated with said (i)th test image;
   comparing by said programmable processor said (i)th test subject response with an (i)th nominal test image response, wherein said (i)th nominal test image response is associated with said (i)th test image, and wherein said (i)th nominal test image response comprises one of said plurality of nominal test image responses;
   determining by said programmable processor an (i)th likelihood of test subject colorblindness based upon said comparison between said (i)th test subject response and said (i)th nominal test image response;
   operative if said (i)th likelihood of test subject colorblindness is greater than said low likelihood of colorblindness threshold, and if said (i)th likelihood of test subject colorblindness is less than said high likelihood of colorblindness threshold, selecting by said programmable processor an (i+1)th test image based upon said comparison between said (i)th test subject response and said (i)th nominal test image response, wherein said (i+1)th test image comprises one of said plurality of test images;
   operative if said (i)th likelihood of test subject colorblindness is less than or equal to said low likelihood of colorblindness threshold, ending said colorblindness test and generating by said programmable processor test results reciting a low likelihood of test subject colorblindness; and
   operative if said (i)th likelihood of test subject colorblindness is greater than or equal to said high likelihood of colorblindness threshold, ending said colorblindness test and generating by said programmable processor test results reciting a high likelihood of test subject colorblindness.

2. The computer implemented method of claim 1, wherein said selecting step further comprising selecting an (i+1)th test image randomly from said plurality of test images.

3. The computer implemented method of claim 1, wherein said selecting step further comprises selecting a test image type from the group consisting of Ishihara plates, HRR plates, and Farnsworth color disks.

4. The computer implemented method of claim 1, wherein said computing device further comprises one or more nominal light intensity values encoded in said computer readable medium, said method further comprising:
   measuring one or more ambient light intensities;
   forming one or more comparisons between said one or more measured ambient light intensities and said one or more nominal ambient light intensities,
   adjusting the intensity of said displayed test images based upon said one or more comparisons.

5. The computer implemented method of claim 4, wherein:
   said test apparatus further comprises an optical sensor in communication with said programmable processor; and
   said optical sensor performs said measuring.

6. The computer implemented method of claim 5, further comprising:
   displaying said (i)th test image on the visual display device at a first intensity; and
   displaying said (i+1)th test image on the visual display device at a second intensity; wherein the first intensity differs from the second intensity.

7. An article of manufacture comprising a visual display device, a programmable processor, a computer readable medium, a plurality of test images encoded in said computer readable medium, a plurality of nominal test image responses encoded in said computer readable medium, wherein a nominal test image response is associated with each of said plurality of test images comprising computer, a low likelihood of colorblindness threshold encoded in said computer readable medium, a high likelihood of colorblindness threshold encoded in said computer readable medium, and readable program code to create, display, and evaluate, a test for colorblindness, encoded in said computer readable medium, the computer readable program code comprising a series of computer readable program steps to effect:
   displaying using said visual display device an (i)th test image, wherein (i) is initially set to 1, and wherein said (i)th test image comprises one of said plurality of test images;
   receiving an (i)th test subject response associated with said (i)th test image;
   comparing said (i)th test subject response with an (i)th nominal test image response, wherein said (i)th nominal test image response is associated with said (i)th test image, and wherein said (i)th nominal test image response comprises one of said plurality of nominal test image responses;
   determining an (i)th likelihood of test subject colorblindness based upon said comparison between said (i)th test subject response and said (i)th nominal test image response;
   operative if said (i)th likelihood of test subject colorblindness is greater than said low likelihood of colorblindness threshold, and if said (i)th likelihood of test subject colorblindness is less than said high likelihood of colorblindness threshold, selecting an (i+1)th test image based upon said comparison between said (i)th test subject response and said (i)th nominal test image response, wherein said (i+1)th test image comprises one of said plurality of test images;

operative if said (i)th likelihood of test subject colorblindness is less than or equal to said low likelihood of colorblindness threshold, ending said colorblindness test and generating a test results reciting a low likelihood of test subject colorblindness; and operative if said (i)th likelihood of test subject colorblindness is greater than or equal to said high likelihood of colorblindness threshold, ending said colorblindness test and generating by said programmable processor test results reciting a high likelihood of test subject colorblindness.

8. The article of manufacture of claim 7, wherein said computer readable program code to select an (i+1)th test image further comprises a series of computer readable program steps to effect selecting an (i+1)th test image randomly from said plurality of test images.

9. The article of manufacture of claim 7, wherein said computer readable program code to select an (i+1)th test image further comprises a series of computer readable program steps to effect selecting a test image type from the group consisting of Ishihara plates, HRR plates, and Farnsworth color disks.

10. The article of manufacture of claim 7, further comprising one or more nominal light intensity values encoded in said computer readable medium, the computer readable program code further comprising a series of computer readable program steps to effect:

measuring one or more ambient light intensities;

forming one or more comparisons between said one or more measured ambient light intensities and said one or more nominal ambient light intensities; and adjusting the intensity of said displayed test images based upon said one or more comparisons.

11. The article of manufacture of claim 10, further comprising an optical sensor in communication with said programmable processor, wherein said computer readable program code to measure one or more ambient light intensities further comprises a series of computer readable program steps to effect measuring one or more ambient light intensities using said optical sensor.

12. The article of manufacture claim 10, the computer readable program code further comprising a series of computer readable program steps to effect:

displaying said (i)th test image on the visual display device at a first intensity; and displaying said (i+1)th test image on the visual display device at a second intensity;

wherein the first intensity differs from the second intensity.

13. A computer program product encoded in a computer readable medium and usable with a programmable computer processor disposed in a computing device in communication with a visual display device and further comprising a plurality of test images encoded in said computer readable medium, a plurality of nominal test image responses encoded in said computer readable medium, wherein a nominal test image response is associated with each of said plurality of test images comprising computer, a low likelihood of colorblindness threshold encoded in the computer readable medium, and a high likelihood of colorblindness threshold encoded in the computer readable medium, the computer program product comprising:

computer readable program code which causes said programmable processor to display using said visual display device an (i)th test image, wherein (i) is initially set to 1, and wherein said (i)th test image comprises one of said plurality of test images;

computer readable program code which causes said programmable processor to receive an (i)th test subject response associated with said (i)th test image;

computer readable program code which causes said programmable processor to compare said (i)th test subject response with an (i)th nominal test image response, wherein said (i)th nominal test image response is associated with said (i)th test image, and wherein said (i)th nominal test image response comprises one of said plurality of nominal test image responses;

computer readable program code which causes said programmable processor to determine an (i)th likelihood of test subject colorblindness based upon said comparison between said (i)th test subject response and said (i)th nominal test image response;

computer readable program code which, if said (i)th likelihood of test subject colorblindness is greater than said low likelihood of colorblindness threshold, and if said (i)th likelihood of test subject colorblindness is less than said high likelihood of colorblindness threshold, causes said programmable processor to select an (i+1)th test image based upon said comparison between said (i)th test subject response and said (i)th nominal test image response, wherein said (i+1)th test image comprises one of said plurality of test images;

computer readable program code which, if said (i)th likelihood of test subject colorblindness is less than or equal to said low likelihood of colorblindness threshold, causes said programmable processor to end said colorblindness test and generate test results reciting a low likelihood of test subject colorblindness; and computer readable program code which, if said (i)th likelihood of test subject colorblindness is greater than or equal to said high likelihood of colorblindness threshold, causes said programmable processor to end said colorblindness test and generate test results reciting a high likelihood of test subject colorblindness.

14. The computer program product of claim 13, wherein said computer readable program code to select an (i+1)th test image further comprises computer readable program code which causes said programmable processor to select an (i+1)th test image randomly from said plurality of test images.

15. The computer program product of claim 13, wherein said computer readable program code to select an (i+1)th test image further comprises computer readable program code which causes said programmable processor to select a test image type from the group consisting of Ishihara plates, HRR plates, and Farnsworth color disks.

16. The computer program product of claim 13, wherein said computing device further comprises one or more nominal light intensity values encoded in said computer readable medium, further comprising:

computer readable program code which causes said programmable processor to measure one or more ambient light intensities;

computer readable program code which causes said programmable processor to form one or more comparisons between said one or more measured ambient light intensities and said one or more nominal ambient light intensities; and computer readable program code which causes said programmable processor to adjust the intensity of said displayed test images based upon said one or more comparisons.

17. The computer program product claim 13, further comprising:
   computer readable program code which causes said programmable processor to display said (i)th test image on the visual display device at a first intensity; and
   computer readable program code which causes said programmable processor to display said (i+1)th test image on the visual display device at a second intensity;
   wherein the first intensity differs from the second intensity.

* * * * *